United States Patent
Nakamura et al.

(10) Patent No.: US 11,493,467 B2
(45) Date of Patent: Nov. 8, 2022

(54) SENSOR FOR DETECTING A CHANGE OF RESISTANCE BETWEEN A PAIR OF ELECTRODES

(71) Applicant: Nabtesco Corporation, Tokyo (JP)

(72) Inventors: Koji Nakamura, Tsu (JP); Kazuhiko Sakurai, Tsu (JP); Masaki Harada, Tsu (JP); Toshihide Fujii, Tsu (JP)

(73) Assignee: NABTESCO CORPORATION, Tokyo (JP)

( * ) Notice: Subject to any disclaimer, the term of this patent is extended or adjusted under 35 U.S.C. 154(b) by 0 days.

(21) Appl. No.: 16/189,168

(22) Filed: Nov. 13, 2018

(65) Prior Publication Data
US 2019/0154608 A1 May 23, 2019

(30) Foreign Application Priority Data

Nov. 22, 2017 (JP) .............................. JP2017-224585

(51) Int. Cl.
*G01N 27/07* (2006.01)
*G01N 33/28* (2006.01)

(52) U.S. Cl.
CPC ......... *G01N 27/07* (2013.01); *G01N 33/2858* (2013.01); *G01N 33/2888* (2013.01)

(58) Field of Classification Search
CPC . G01N 27/07; G01N 33/2888; G01N 33/2858
See application file for complete search history.

(56) References Cited

U.S. PATENT DOCUMENTS

| 4,015,199 A | * | 3/1977 | Rommel | ................. G01N 27/07 324/439 |
| 4,087,764 A | * | 5/1978 | Young | ................... H01S 3/0632 372/20 |
| 5,089,780 A | * | 2/1992 | Megerle | ............. G01N 33/2888 324/444 |

(Continued)

FOREIGN PATENT DOCUMENTS

JP 62-034355 U 2/1987
JP 2005-331324 A 12/2005
(Continued)

OTHER PUBLICATIONS

Notification of First Office Action dated Aug. 4, 2021, issued in corresponding Chinese Patent Application No. 201811391558.1 with English translation.
(Continued)

*Primary Examiner* — Jeff W Natalini
(74) *Attorney, Agent, or Firm* — Pillsbury Winthrop Shaw Pittman, LLP

(57) ABSTRACT

Provided is a sensor that can appropriately sense the amount of abrasion powder (conductive substance) in a mechanical device of any size, and thereby to provide a sensor that can be generally used for preventive maintenance of any mechanical parts. The sensor includes a first electrode and a second electrode. A voltage is applied between the first electrode and the second electrode to accumulate conductive substance between the first and second electrodes in order to sense a decrease in electric resistance between the first and second electrodes. The distance between the first electrode and the second electrode is adjustable.

22 Claims, 11 Drawing Sheets

(56) References Cited

U.S. PATENT DOCUMENTS

| | | | | |
|---|---|---|---|---|
| 2005/0112544 A1* | 5/2005 | Xu | ................ | C12M 23/12 |
| | | | | 435/4 |
| 2005/0266571 A1* | 12/2005 | Stout | ................ | A61B 5/14514 |
| | | | | 436/55 |
| 2016/0178449 A1* | 6/2016 | Goedel | ................ | G01K 7/16 |
| | | | | 374/185 |
| 2016/0363347 A1* | 12/2016 | Chaudhry | ................ | F24H 1/202 |
| 2017/0138877 A1* | 5/2017 | Otomaru | ................ | G01N 15/06 |

FOREIGN PATENT DOCUMENTS

| | | | | |
|---|---|---|---|---|
| JP | 2010-014518 A | 1/2010 | | |
| JP | 2012-078130 A | 4/2012 | | |
| JP | 2012078130 | * | 4/2012 | ............ F01N 3/023 |

OTHER PUBLICATIONS

Notice of Reasons for Refusal dated Dec. 7, 2021, issued in corresponding Japanese Patent Application No. 2017-224585 with English translation (12 pgs.).

Non-Final Office Action dated Jun. 17, 2022, issued in corresponding Taiwanese Patent Application No. 107141678 with English translation (10 pgs.).

* cited by examiner

SENSOR FOR DETECTING A CHANGE OF RESISTANCE BETWEEN A PAIR OF ELECTRODES

CROSS-REFERENCE TO RELATED APPLICATIONS

This application is based on and claims the benefit of priority from Japanese Patent Application Serial No. 2017-224585 (filed on Nov. 22, 2017), the contents of which are hereby incorporated by reference in its entirety.

TECHNICAL FIELD

The present disclosure relates to a sensor.

BACKGROUND

A mechanical device such as a speed reducer is usually housed in a housing filled with lubricant so as to prevent damage to mechanical parts such as gears and bearings. When mechanical parts are worn during operation of the mechanical device, abrasion powder (mainly conductive substance such as iron powder) is contained in the lubricant.

In general, when wear of mechanical parts advances into a wear-out failure period in a failure rate curve (a bathtub curve), a larger amount of abrasion powder (conductive substance) is generated and contained in the lubricant. In order to accurately perform preventive maintenance of the mechanical parts, it is needed to appropriately detect increase in the amount of generated abrasion powder (conductive substance).

For example, Japanese Patent Application Publication No. 2005-331324 ("the '324 Publication") discloses a sensor that senses the amount of metal powder in oil. The sensor of the '324 Publication includes: a sensor head having a permanent magnet; a cup-shaped electrode provided on a distal end surface of the sensor head; and a plurality of rod-shaped conductive members arranged on an outer peripheral surface of the sensor head. The '324 Publication describes that an output of the sensor is varied when a short circuit occurs between rod-shaped conductive members due to the abrasion powder accumulated between opposed end surfaces of the conductive members (a sensing region) and the cup-shaped electrode subjected to a magnetic field by a permanent magnet. The sensor utilizes this to sense a degree of contamination of the oil However, since mechanical devices have various sizes from small to large, and sizes of mechanical components in the devices also largely vary so that the amount of abrasion powder (conductive substance) generated during operation also varies depending on the devices. For the sensor as described in the '324 Publication, to perform preventive maintenance of mechanical parts, it is necessary to design and develop the sensor to fit it to each target mechanical device, and it is difficult to general-adapt the sensor to the mechanical devices having various sizes.

SUMMARY

The invention is made in view of the above drawback, and it is an object of the invention to provide a sensor that can appropriately sense the amount of abrasion powder (conductive substance) in a mechanical device of any size, and thereby to provide a sensor that can be generally used for preventive maintenance of any mechanical parts.

A sensor according to one embodiment includes a first electrode and a second electrode. A voltage is applied between the first electrode and the second electrode to accumulate conductive substance between the first and second electrodes in order to sense a change in electric resistance between the first and second electrodes. The distance between the first electrode and the second electrode is adjustable.

In the sensor according to one embodiment, at least one of the first electrode or the second electrode is configured to be replaceable.

In the sensor according to one embodiment, at least one of the first electrode or the second electrode is replaceable with an electrode having a different size, and the distance between the first electrode and the second electrode is configured to be adjustable.

In the sensor according to one embodiment, at least one of the first electrode or the second electrode has a tapered surface facing the other of the first electrode or the second electrode.

In the sensor according to one embodiment, one of the first electrode or the second electrode is threadably attached to the other of the first electrode or the second electrode, and a spring is provided between the one of the first electrode or the second electrode and the other of the first electrode or the second electrode.

In the sensor described above, when the threaded state between the one and the other of the first electrode or the second electrode is loosened, the other of the first electrode or the second electrode may be moved by the spring in an extending direction of the spring.

In the sensor according to one embodiment, an end portion of at least one of the first electrode or the second electrode facing the other of the first electrode or the second electrode and facing toward a direction from which the conductive substance approaches there to is chamfered.

In the sensor according to one embodiment, a resin material is filled in a region other than a region where the conductive substance is accumulated between the electrodes.

According to another aspect of the invention, provided is a machinery for housing a device. The machinery includes a flange, and the above-described sensor is attached to a case, and the case is fixed to the flange in a secured manner.

In the machinery according to one embodiment, at least a portion of the case contacting the flange is formed of insulating material In the machinery according to one embodiment, the sensor is detachably fixed to the flange.

In the machinery according to one embodiment, an end surface of the case contacting the flange is threadably fixed to an end surface of the flange.

In the machinery according to one embodiment, the device is a speed reducer.

With the sensor according to one embodiment, it is possible to appropriately sense the amount of abrasion powder (conductive substance) in a mechanical device of any size, and thereby the sensor can be generally used for preventive maintenance of any mechanical parts.

DESCRIPTION OF THE EMBODIMENTS

Embodiments of the invention will now be described with reference to the appended drawings. The following description will be focused on a speed reducer as an example of a device according to embodiments of the invention.

Figure 1:
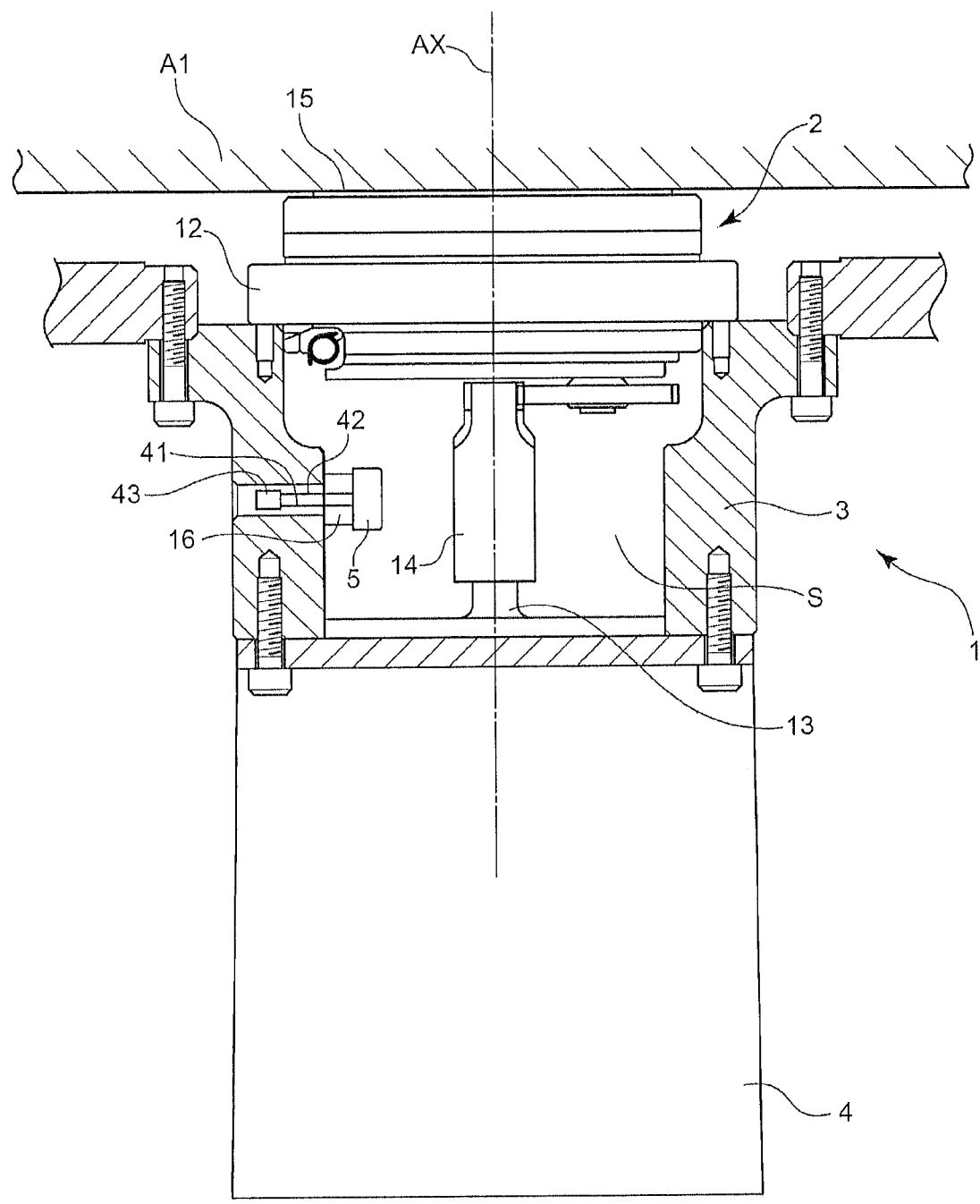
FIG. 1 is a side view of a machinery 1 according to an embodiment of the invention.

FIG. 1 is a side view of a machinery 1 according to an embodiment of the invention. Referring to FIG. 2, the machinery 1 includes a flange 3. At least a part of a speed reducer 2 is housed in the flange 3.

The flange 3 is a housing member for housing the reducer 2, and a servo motor 4 is attached to the flange 3. The flange 3 is a substantially tubular member having a hollow portion (a space S). The openings of the flange 3 at both axial ends thereof are closed by the speed reducer 2 and the servo motor 4, and thus the closed space S is formed. The space S is filled with a lubricant, and the flange 3 also serves as an oil bath.

The speed reducer 2 includes a case 12 mounted to the flange 3, an input shaft 14 connected to an output shaft 13 of the servo motor 4, and an output shaft 15. The input shaft 14 and the output shaft 15 are supported so as to be rotatable about the rotational axis AX relative to the case 12. The case 12 is provided on the flange 3 in an airtight manner.

Output of the servo motor 4 is input to the speed reducer 2 via the input shaft 14, reduced by the speed reducer 2, and then transmitted to an output-side device A1 via the output shaft 15.

A space in the case 12 that houses a gear mechanism of the speed reducer 2 communicates with the space S in the flange 3. During operation of the speed reducer 2, rotation of the gear mechanism in the case 12 causes the lubricant to be circulated between the space in the case 12 and the space S in the flange 3. As the lubricant is circulated, the abrasion powder (hereinafter referred to as the conductive substance) generated in the speed reducer 2 is discharged into the space S in the flange 3.

In the space S, a sensor 5 for sensing an increase of the amount of the conductive substance floating in the lubricant is mounted on a support member 16. A magnet of the sensor 5 causes the conductive substance to be accumulated in a gap between electrodes and the sensor 5 detects the amount of the abrasion powder in the lubricant by sensing a change in the electric resistance between the electrodes. There may be a plurality of variations of the sensor 5. With reference to FIGS. 2 to 6, embodiments of some types of the sensor 5 will be described. Here, the sensor 5 may be arranged inside the case 12, and may be adequately arranged at any place in the machinery 1.

Figure 2A:
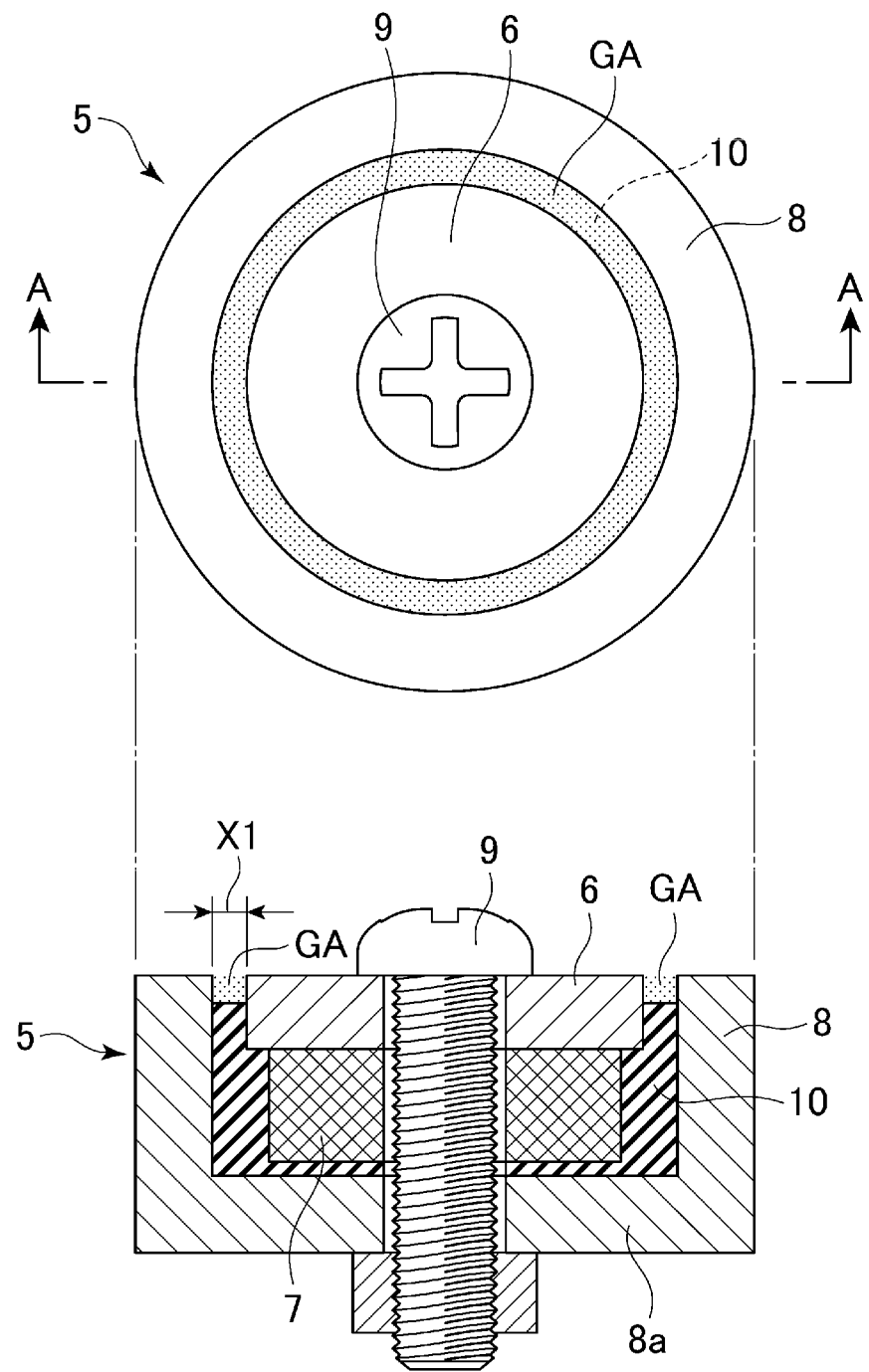
FIGS. 2a to 2c are side and top views of a sensor 5 according to an embodiment of the invention.
Figure 2B:
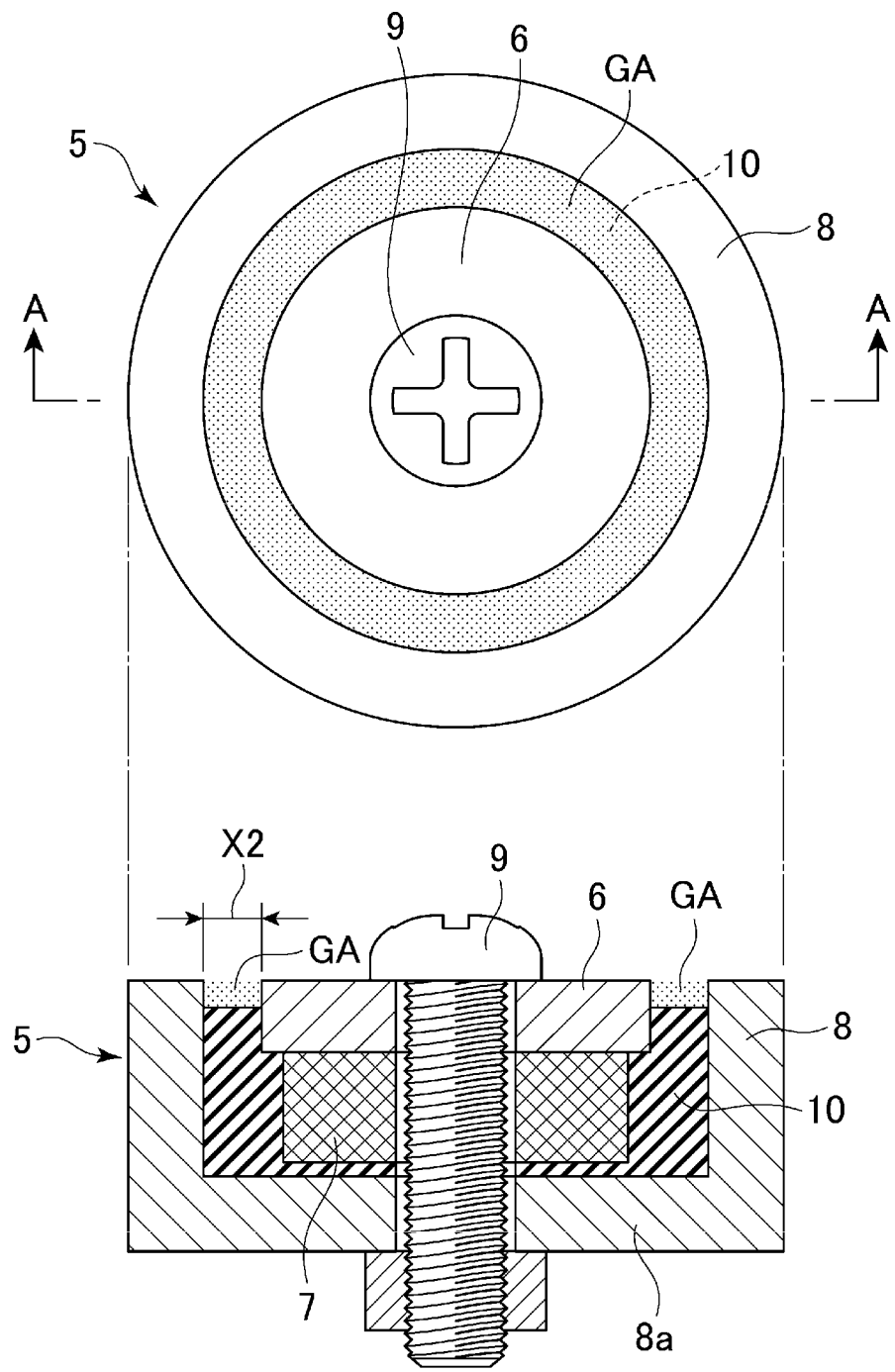
Figure 2C:
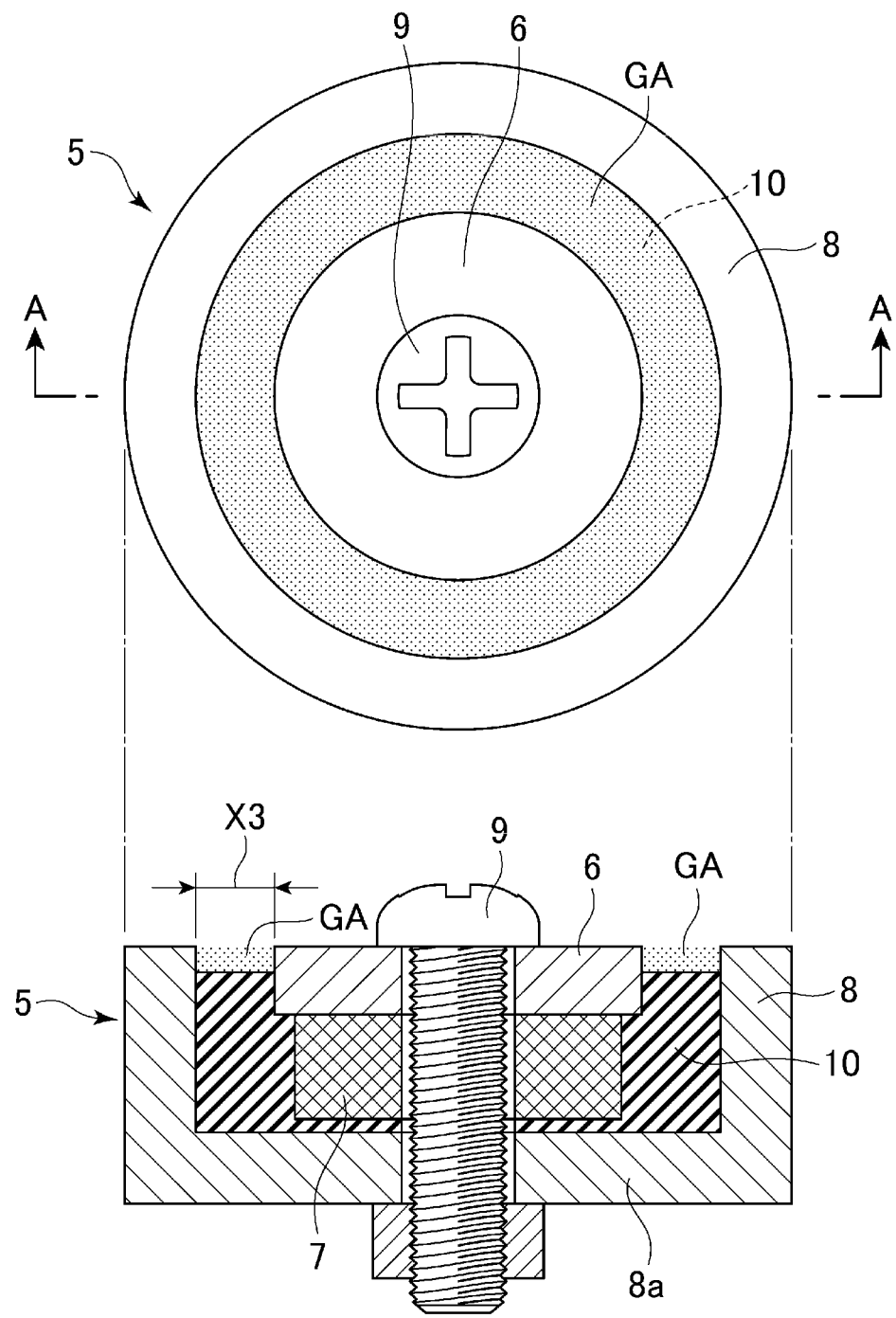

FIGS. 2a to 2c illustrate the sensor 5 according to an embodiment of the invention. FIGS. 2a to 2c each show a top view of the sensor 5 and a cross-sectional view taken along the line A-A of the top view.

As shown in FIGS. 2a to 2c, the sensor 5 includes a center electrode (first electrode) 6, a permanent magnet 7, a box-shaped electrode (second electrode) 8, a screw 9, and a resin material 10. As shown in the drawing, the center electrode (first electrode) 6 and the permanent magnet 7 are fixed to the box-shaped electrode (second electrode) 8 by the screw 9. A signal line 41 shown in FIG. 1 is connected to the box-shaped electrode 8, and the signal line 42 is connected to the center electrode 6. It should be noted that the permanent magnet 7 may not be used and the center electrode 6 may be configured to serve as the magnet and the electrode.

The box-shaped electrode 8 is a magnetic member formed of a magnetic material having electric conductivity such as iron, ferrite, or silicon steel. The box-shaped electrode 8 has a substantially cylindrical shape and its opening is closed on one end in the axial direction (the bottom in FIG. 3d) with a bottom portion 8a. Thus the box-shaped electrode 8 has a cylindrical box-shaped shape with an opening at the top. Alternatively, the shape of the box-shaped electrode 8 may be a rectangular parallelepiped with the opened top thereof or a polygonal tube with a closed bottom.

In the hollowed portion of the box-shaped electrode 8, there is disposed a resin material 10, which is a nonmagnetic material (an insulator). In this manner, the center electrode (first electrode) 6 and the permanent magnet 7 are formed such that at least a part of them are buried in the central region of the resin material That is, the box-shaped electrode 8 is arranged so as to surround the resin material 10 in which at least a part of the permanent magnet 7 and the box-shaped electrode 8 are buried. The shapes of the permanent magnet 7 and the center electrode 6 are not limited to cylindrical shapes but may be a rectangular parallelepiped, a polygonal column, or the like.

As shown in each sectional view of FIGS. 2a to 2c, the outer shape of the center electrode 6 is formed such that it is smaller than the inner periphery of the box-shaped electrode 8. Accordingly, a gap GA is formed between the center electrode 6 and the box-shaped electrode 8 over the entire periphery of the center electrode 6 (so as to surround the center electrode) on the resin material 10. In other words, the center electrode 6 and the box-shaped electrode 8 are arranged so as to face each other with the gap GA on the resin material 10 interposed therebetween as the center.

Output lines (signal lines 41, 42 shown in FIG. 1) are connected to the center electrode 6 and the box-shaped electrode 8 respectively. As shown in the figure, the permanent magnet 7 may be attached to the lower part of the center electrode 6 or the like, or it may not be so. In addition, when the permanent magnet 7 is attached, the permanent magnet 7 is formed of magnet or an electromagnet, but it is preferable that the magnet be covered with a nonmagnetic material such as copper and the signal line 41 or the signal line 42 be connected to the covering layer.

The output ends of the output lines are coupled to a sensor drive circuit (not shown) that monitors a resistance value of the sensor 5 to predict a failure of the mechanical parts based on variation of the resistance value due to the accumulation of the conductive substance between the electrodes. The sensor circuit is one example of a sensing means that detects a change in electric resistance between the center electrode 6 and the box-shaped electrode 8. The sensing means may be configured to sense a decrease in the electric resistance between the center electrode 6 and the box-shaped electrode 8. As such a sensing means, a commercially available Ohmmeter can be used. When a certain amount of conductor substance accumulates in the gap GA, the electric resistance between the center electrode 6 to which a voltage is applied and the box-shaped electrode 8 decreases, and output levels of the output lines change. The sensor drive circuit utilizes detection of the decrease in the electric resistance to predict a failure of the mechanical parts. The decrease in the electric signal includes an ON signal (with electricity passing) and an OFF signal (with no electricity passing) so that it is also possible to perform sensing between these ON and OFF states (hereinafter referred to as "digital sensing").

The sensor driving circuit is connected to a superior control device such as a manipulator in a wired or wireless manner. A circuit board 43 in FIG. 1 may transmit outputs of the output lines (an output of the sensor 40A) to an upper-level control device either constantly or intermittently (at regular time intervals) for saving electricity.

When sensing the variation of the output levels of the output lines received from the circuit board 43, the upper-level control device may give an alert for demanding maintenance of, for example, the speed reducer 2 with a predetermined notification means (a display or a voice output device).

The permanent magnet 8 is magnetized, and a magnetic flux path cpA is formed in a predetermined direction. In particular, a strong magnetic flux flows in the gap GA around the center electrode 6. By a magnetic force of the permanent magnet 7, conductive substance of mechanical parts (for example, conductive substance from mechanical parts mixed in the lubricant) is attracted in the gap GA.

Here, as wear of mechanical parts advances into the wear-out failure period in the failure rate curve (the bathtub curve), the amount of generated conductive substance increases, but this generation amount greatly differs depending on the size of the device. In general, the larger the device is, the greater the number of or the larger the size of its conductor parts is, so that more conductive substance is generated. Therefore, in a large device, more conductive substance is generated until the wear of its mechanical parts progresses and enters the wear failure period.

For this reason, if sensors having the same gap GA are simply used for devices having different failure rate curves, preventive maintenance of their mechanical parts of the devices with various sizes cannot be performed accurately. However, the sensor 5 in one embodiment of the invention may be configured to have different gap GA lengths (X1, X2, X3), as shown in FIGS. 2a, 2b and 2c. Therefore, by selecting the sensor 5 having an appropriate gap GA length according to the size of the target device, preventive maintenance tailored to the failure rate curve of the device can be performed.

More specifically, as shown in the drawing, in the sensor 5 in one embodiment, the center electrode 6 and the permanent magnet 7 are fixed to the box-shaped electrode 8 having various radial dimensions by the screw 9. Therefore it is possible to configure the sensor 5 in which the gap GA has an appropriate length according to the size of the target device.

Further, in the sensor 5 according to the embodiment of the invention, the center electrode 6 and the permanent magnet 7 having different radial dimension may be fixed to the box-shaped electrode 8 by the screw 9. This makes it possible to configure the sensor 5 having an appropriate gap GA length that matches the size of the target device.

Figure 3A:
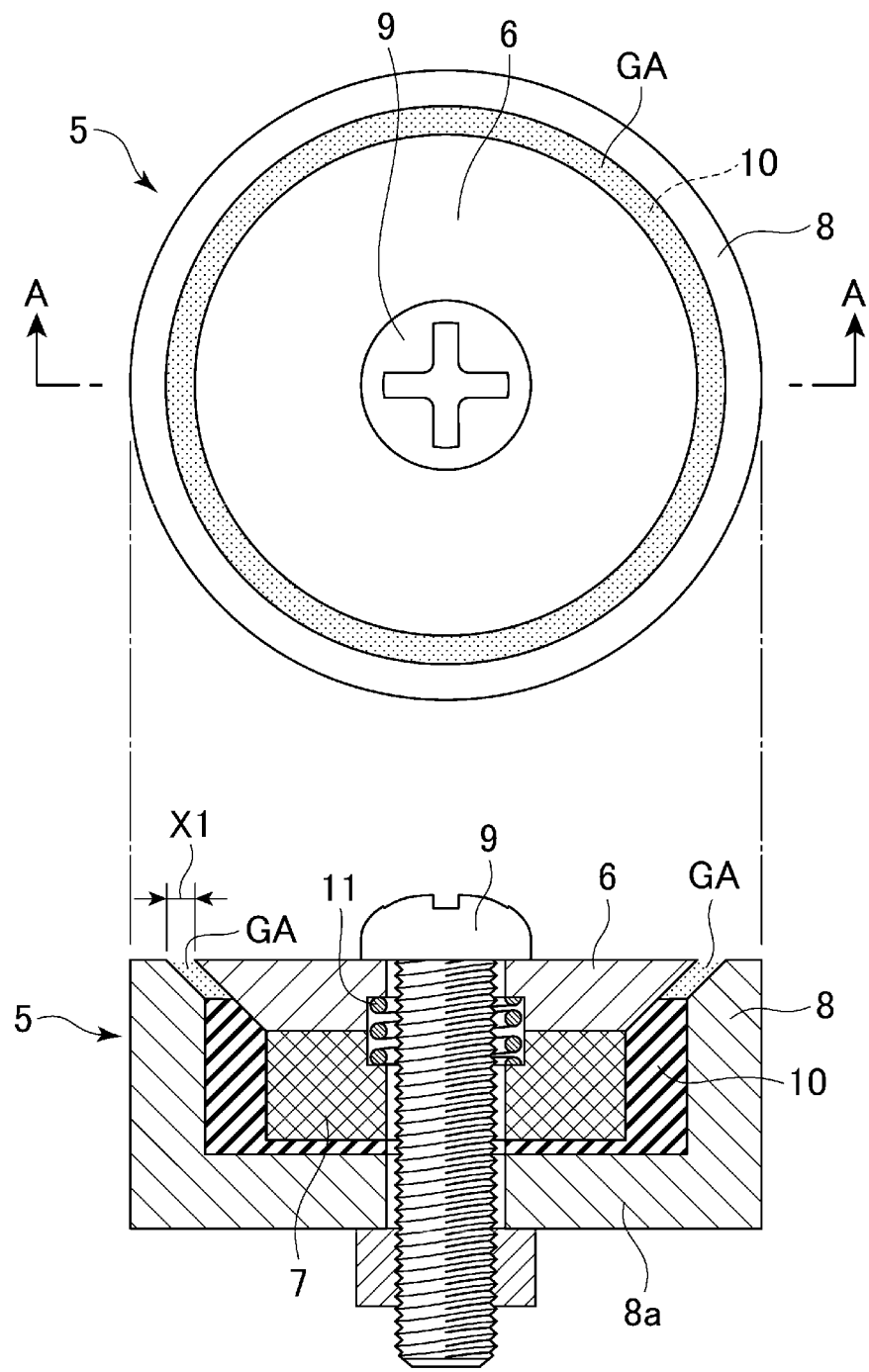
FIGS. 3a and 3b show a configuration of a sensor according to a first embodiment of the invention.
Figure 3B:
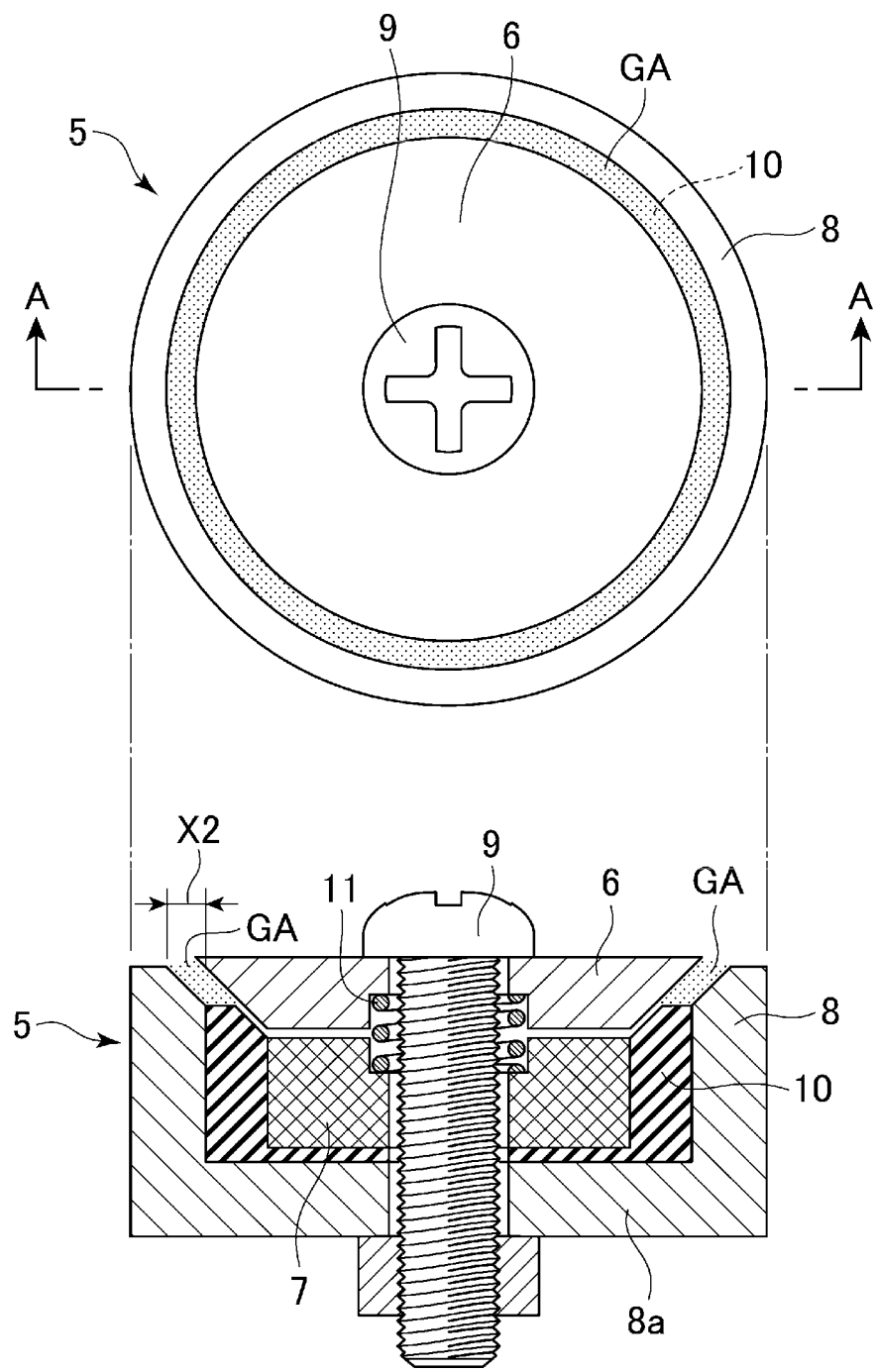

FIGS. 3a and 3b show the sensor 5 according to another embodiment of the invention. FIG. 3a shows a top view and a cross-sectional view taken along the line A-A. FIG. 3b shows a cross sectional view taken along the line A-A in another state.

As shown in FIG. 3a, the sensor 5 includes the center electrode (first electrode) 6, the permanent magnet 7, the box-shaped electrode (second electrode) 8, a spring 11, the screw 9, and the resin material 10. As shown in the drawing, the spring 11 is provided between the center electrode (first electrode) 6 and the permanent magnet 7, and they are fixed to the box-shaped electrode (second electrode) 8 by the screw 9. Although not shown in the drawings, the signal line 41 shown in FIG. 1 is connected to the box-shaped electrode 8, and the signal line 42 is connected to the center electrode 6. It should be noted that the permanent magnet 7 may not be used and the center electrode 6 may be configured to serve as the magnet and the electrode.

The box-shaped electrode 8 is a magnetic member formed of a magnetic material having electric conductivity such as iron, ferrite, or silicon steel The box-shaped electrode 8 has a substantially cylindrical shape and its opening is closed on one end in the axial direction (the bottom in the sectional view of FIG. 3a) with a bottom portion 8a. Thus the box-shaped electrode 8 has a cylindrical box-shaped shape with an opening at the top. Alternatively, the shape of the box-shaped electrode 8 may be a rectangular parallelepiped with the opened top thereof or a polygonal tube with a closed bottom.

In the hollowed portion of the box-shaped electrode 8, there is disposed a resin material 10, which is a non-magnetic material (an insulator). In this manner, the center electrode (first electrode) 6 and the permanent magnet 7 are formed such that at least a part of them are buried in the central region of the resin material That is, the box-shaped electrode 8 is arranged so as to surround the resin material 10 in which at least a part of the permanent magnet 7 and the box-shaped electrode 8 are buried. The shapes of the permanent magnet 7 and the center electrode 6 are not limited to cylindrical shapes but may be a rectangular parallelepiped, a polygonal column, or the like.

As shown in each sectional view of FIGS. 3a and 3b, the outer shape of the center electrode 6 is formed such that it is smaller than the inner periphery of the box-shaped electrode 8 and tapered downward in the view of FIGS. 3a and 3b. The side of the end portion of the box-shaped electrode 8 facing the center electrode 6 is formed so as to taper upward in the view of FIGS. 3a and 3b. Accordingly, a gap GA is formed between the center electrode 6 and the box-shaped electrode 8 over the entire periphery of the center electrode 6 (so as to surround the center electrode) on the resin material 10. In other words, the center electrode 6 and the box-shaped electrode 8 are arranged so as to face each other with the gap GA on the resin material 10 interposed therebetween as the center.

The output lines (the signal lines 41, 42) are connected to the center electrode 6 and the box-shaped electrode 8 respectively. As shown in the figure, the permanent magnet 7 may be attached to the lower part of the center electrode 6 or the like, or it may not be so. In addition, when the permanent magnet 7 is attached, the permanent magnet 7 is formed of magnet or an electromagnet, but it is preferable that the magnet be covered with a nonmagnetic material such as copper and the signal lines 41, 42 be connected to the covering layer. Other features are generally similar to the embodiment shown in FIGS. 2a to 2c.

As described above, as wear of mechanical parts advances into the wear-out failure period in the failure rate curve (the bathtub curve), the amount of generated conductive substance increases, but this generation amount greatly differs depending on the size of the device. In general, the larger the device is, the greater the number of or the larger the size of its conductor parts is, so that more conductive substance is generated. Therefore, in a large device, more conductive substance is generated until the wear of its mechanical parts progresses and enters the wear failure period.

For this reason, if sensors having the same gap GA are simply used for devices having different failure rate curves, preventive maintenance of their mechanical parts of the devices with various sizes cannot be performed accurately. However, the sensor 5 in one embodiment of the invention may be configured to have the different gap GA lengths X1, X2 as shown in FIGS. 3a and 3b respectively. Therefore, by selecting the sensor 5 having an appropriate gap GA length according to the size of the target device, preventive maintenance tailored to the failure rate curve of the device can be performed.

Specifically, the sensor 5 in one embodiment is configured such that the center electrode 6 and the permanent magnet 7 may be initially fixed by the screw 9 as shown in FIG. 3a, from this state, the spring 11 may be extended in the upward direction of the view of FIG. 3b by loosening the screw 9 thereby moving the center electrode 6 in the same direction in FIG. 3b. In this way, the length X1 of the gap GA in the sensor 5 shown in FIG. 3a is changed to the length X2 of the gap GA in the sensor 5 shown in FIG. 3b thereby it is possible to form a larger gap space.

Figure 4:
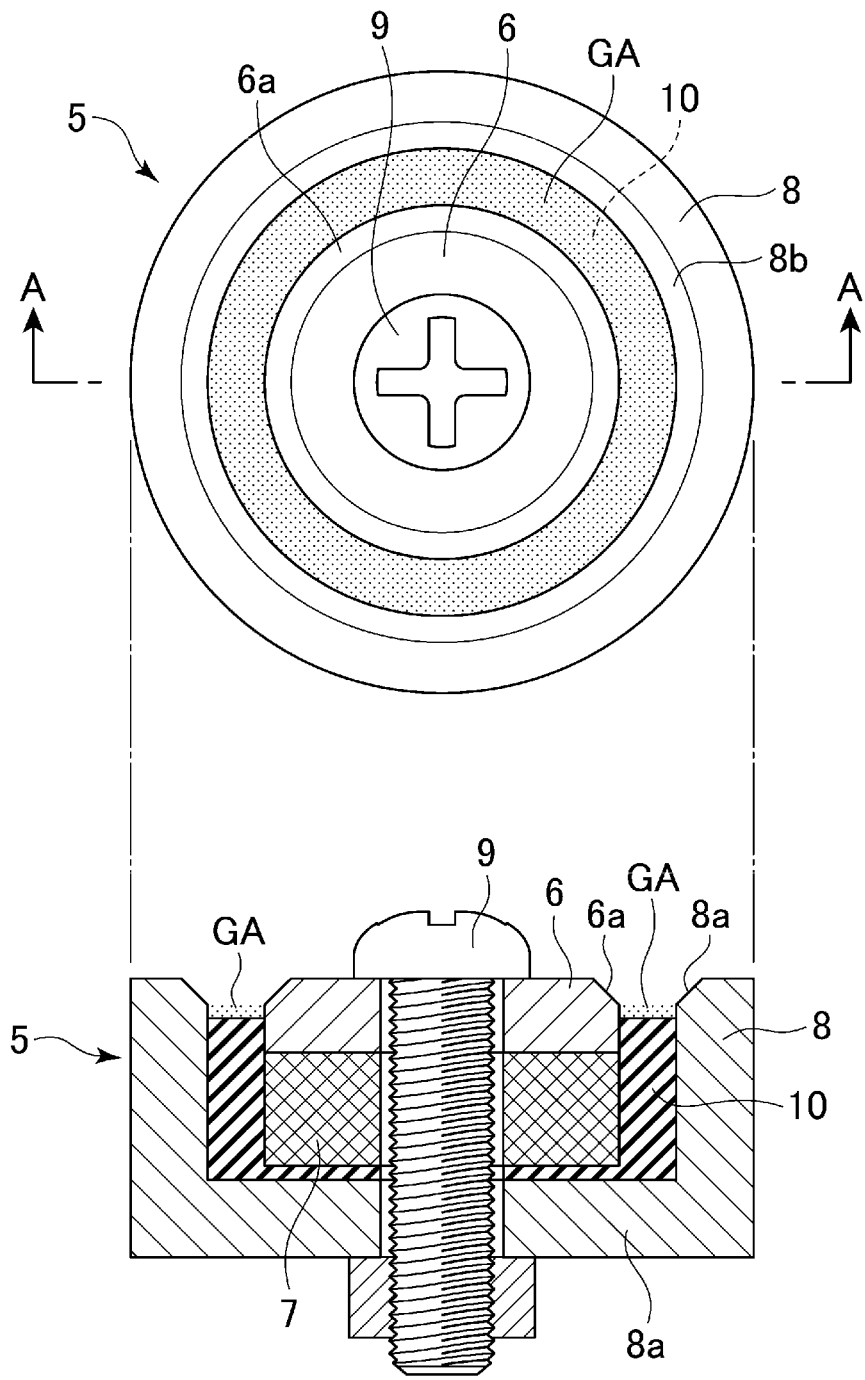
FIG. 4 shows a configuration of a sensor according to a second embodiment of the invention.
Figure 5:
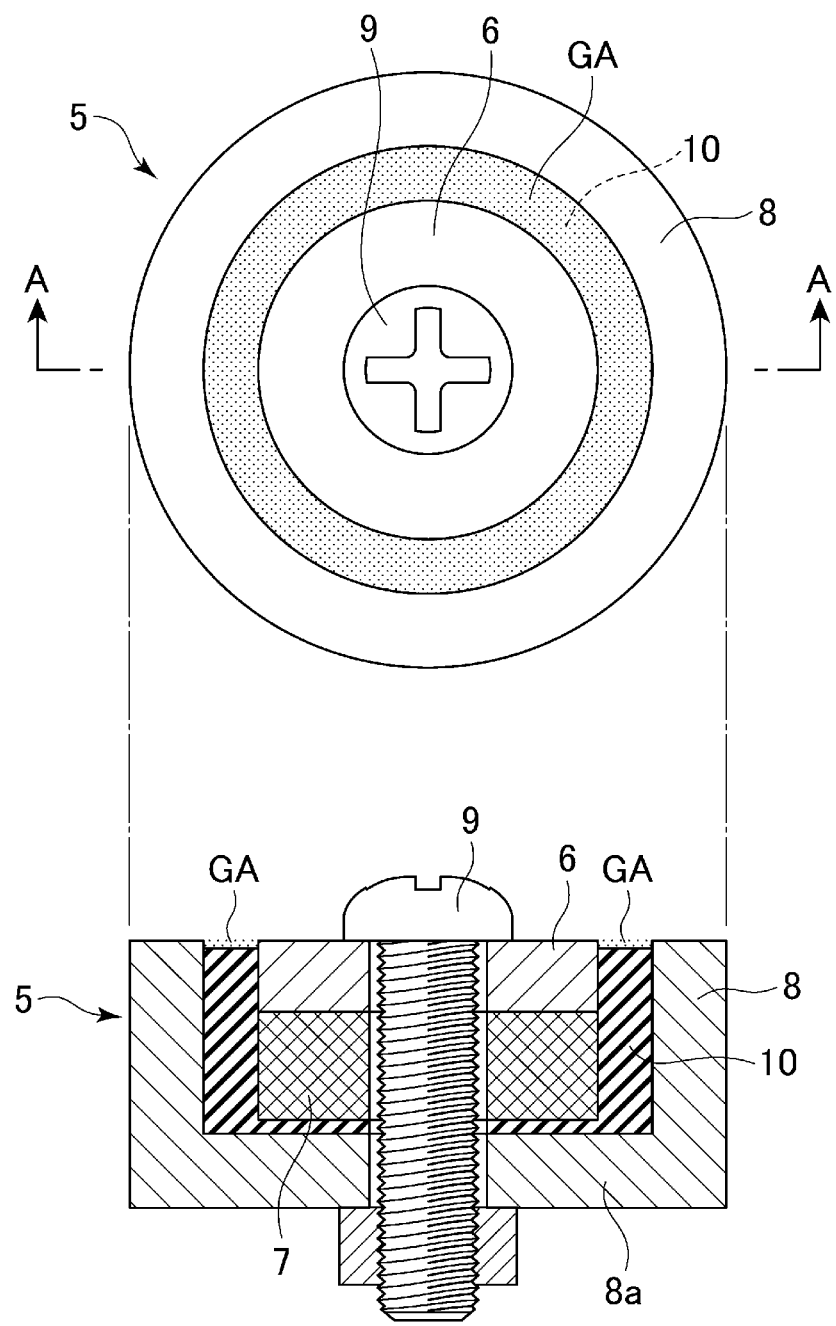
FIG. 5 shows a configuration of a sensor according to a third embodiment of the invention.

FIGS. 4 and 5 show top views of the sensor 5 according to another embodiment of the invention and cross-sectional views taken along the line A-A. Hereinafter, different features of the embodiment compared to the sensor 5 shown in FIGS. 2a to 3b are mainly described.

As shown in FIG. 4, the sensor 5 according to another embodiment includes the center electrode (first electrode) 6, the permanent magnet 7, the box-shaped electrode (second electrode) 8, the screw 9, and the resin material 10. Similar to the sensor 5 shown in FIGS. 2a to 3b, the center electrode (first electrode) 6 and the permanent magnet 7 are fixed to the box-shaped electrode (second electrode) 8 by the screw 9.

In the illustrated example, when viewed in the vertical direction (a direction in which the conductive substance approaches) in FIG. 4, an upper portion (a portion facing toward the direction from which the conductive substance approaches thereto) of the end portion of the center electrode 6 facing the box-shaped electrode 8 is chamfered. Moreover, in the illustrated example, when viewed in the vertical direction (the direction in which the conductive substance approaches) in FIG. 4, an upper portion (a portion facing toward the direction from which the conductive substance approaches thereto) of the end portion of the box-shaped electrode 8 facing the center electrode 6 is chamfered. Both of the end portions may be chamfered as shown in FIG. 4, or one of the end portions may be chamfered.

Since the gap GA of the sensor 5 is recessed circumferentially, when the sensor 5 is inserted into the machinery 1 or the lubricant of the speed reducer 2, bubbles tend to remain in the gap GA due to influence of surface tension or the like, which inhibits accumulation of the conductive substance. However, the chamfered end portions described above makes it difficult for air bubbles to remain in the gap GA, and as a result, the accumulation of the conductive substance is smoothly carried out.

As shown in FIG. 5, the sensor 5 according to another embodiment includes the center electrode (first electrode) 6, the permanent magnet 7, the box-shaped electrode (second electrode) 8, the screw 9, and the resin material 10. Similar to the sensor 5 shown in FIGS. 2a to 3b, the center electrode (first electrode) 6 and the permanent magnet 7 are fixed to the box-shaped electrode (second electrode) 8 by the screw 9.

In the illustrated example, the resin material largely fills in the region, leaving a minimum area for accumulating the conductive substance between the electrodes. Thus, the gap GA as viewed in cross section in the sensor 5 is shallowly formed.

Since the gap GA of the sensor 5 is recessed circumferentially, when the sensor 5 is inserted into the machinery 1 or the lubricant of the speed reducer 2, bubbles tend to remain in the gap GA due to influence of surface tension or the like, which inhibits accumulation of the conductive substance. However, the shallowly formed gap GA as described above makes it difficult for air bubbles to remain in the gap GA, and as a result, the accumulation of the conductive substance is smoothly carried out.

Figure 6:
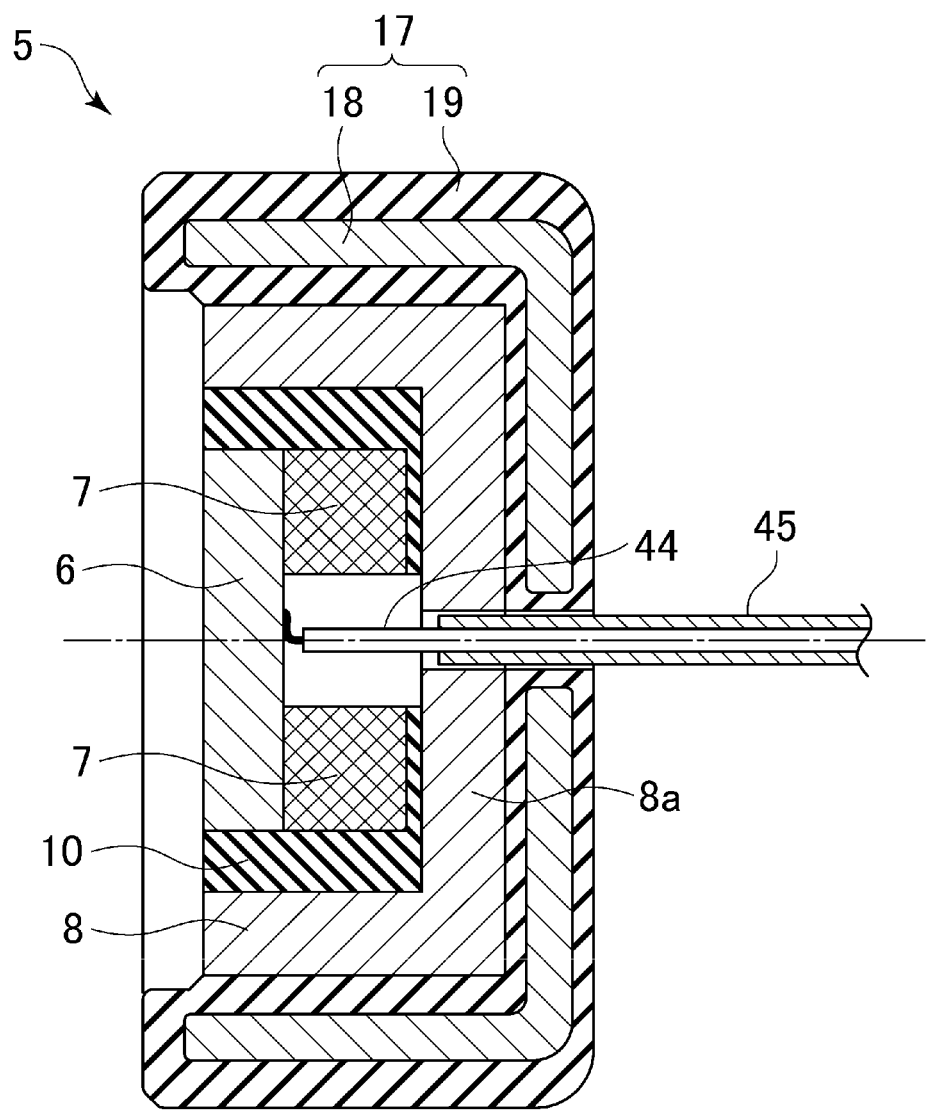
FIG. 6 shows a configuration of a sensor according to a fourth embodiment of the invention.
Figure 7:
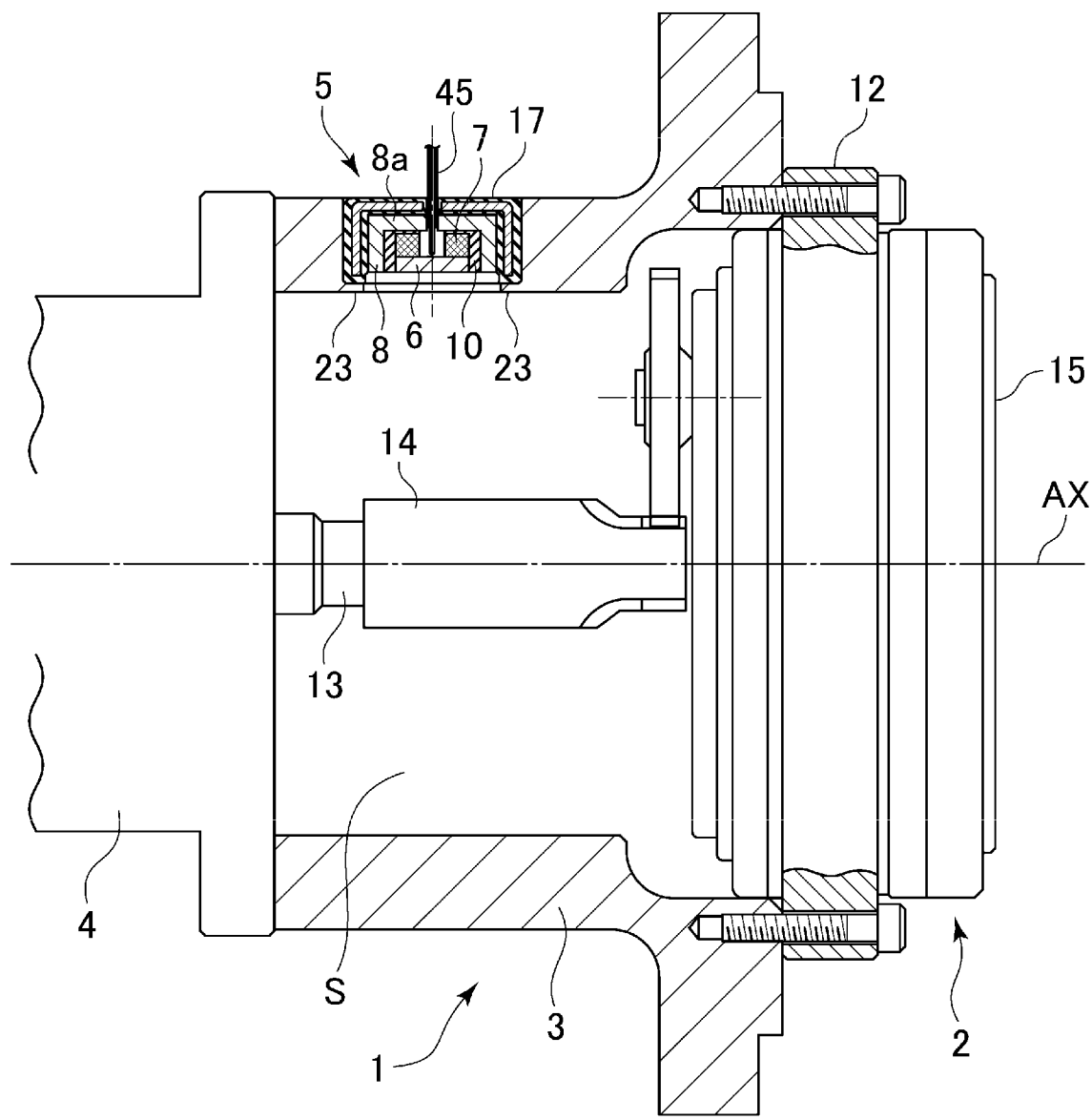
FIG. 7 shows a configuration of a sensor according to a fifth embodiment of the invention.

Meanwhile, the sensor in one embodiment of the invention is required to be configured such that the lubricant does not leak from the sensor itself. FIGS. 6 and 7 are cross-sectional views for explaining such a configuration. As shown in FIG. 6, the sensor 5 includes the center electrode (first electrode) 6, the permanent magnet 7, the box-shaped electrode (second electrode) 8, and the resin material 10, which are surrounded by a sealing member (case) 17.

As shown in the drawing, the center electrode (first electrode) 6, the permanent magnet 7, and the box-shaped electrode (second electrode) 8 are fixed via the resin material 10. The sealing member 17 formed so as to surround the these components includes an inner core metal 18 and an insulating member 19 (for example, a rubber) formed so as to surround the core metal 18 in order to secure a sufficient strength. In the illustrated example, the sealing member 17 is formed in a box shape.

In a central region of a bottom portion 8a of the box-shaped electrode 8 and a central portion of the bottom of the sealing member 17, there is provided an opening for passing a conductive wire. For example, a coaxial cable 44 is used as one type of the conductive wire and the cable is connected by soldering to an end surface of the center electrode 6. The cable is also connected to the bottom portion 8a of the box-shaped electrode 8 via a shield 45 of the coaxial cable 44. In this way, the center electrode 6, the permanent magnet 7, the box-shaped electrode 8, and the coaxial cable 44 are sealed with the resin material 10.

FIG. 7 shows a state in which the sensor 5 configured in this manner is attached to the flange 3 that accommodates the device (for example, the speed reducer 20). As shown in FIG. 7, an opening is formed in the wall of the flange 3 accommodating the speed reducer 20. A sealing member 17 with the sensor 5 attached thereto is inserted in the opening together with the sensor 5, an end surface of the box-shaped sealing member 17 comes in contact with a locking portion 23 of the flange portion 3, and the sealing member is installed in the flange.

Since the outer surface of the sealing member 17 is formed of the insulating member 19, the sensor 5 is insulated from the surroundings when it is attached to the flange 3. In this way, the sensor 5 can be easily attached to the flange 3 of the machinery 1 together with the sealing member 17, and it is unnecessary to separately prepare an insulating member.

When the sensor 5 is fixed as shown in FIG. 7, it is possible to prevent leakage of the lubricant from the place where the sensor 5 is installed and to electrically insulate it from the speed reducer 20 and the flange 3.

Figure 8:
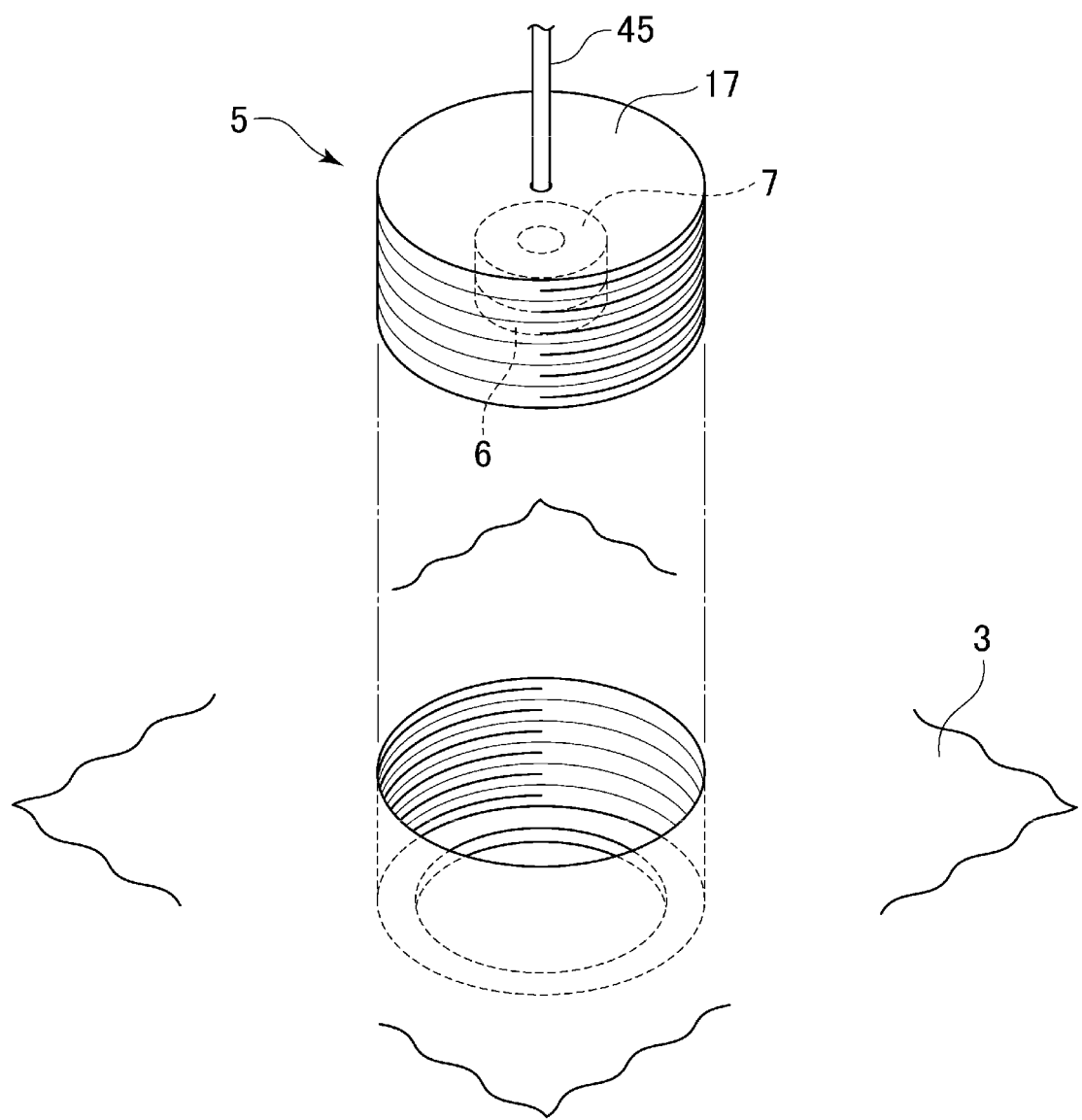
FIG. 8 shows a configuration of a sensor according to a sixth embodiment of the invention.

FIG. 8 shows another fixing method of the sensor shown in FIG. 7. As shown in FIG. 8, the sealing member 17 to which the sensor 5 is attached is detachably fixed to the flange 3 of the machinery 1. More specifically, an end surface of the sealing member 17 that contacts the flange 3 is threadably fixed to the end surface of the opening of the flange 3. Since the outer peripheral surface of the sealing member 17 is threaded like a screw, the sensor 5 can be easily attached to the flange 3 of the machinery 1 together with the sealing member 17.

When the sensor 5 is fixed as shown in FIG. 8, it is possible to prevent leakage of the lubricant from the place where the sensor 5 is installed and it may be configured to be electrically insulate from the speed reducer 20 and the flange 3.

The examples of the embodiments of the present invention have been described above. The embodiments of the invention are not limited to the above examples but can be modified variously within the scope of the technical idea of the present invention. For example, the embodiments of the invention include combinations of the above examples described herein and obvious embodiments.

What is claimed is:

1. A system comprising:
    a sensor comprising:
        a first electrode;
        a second electrode; and
        a detector configured to sense a change in electric resistance between the first electrode and the second electrode when a voltage is applied between the first electrode and the second electrode, and
    a mechanical device to which the sensor is being attached, the mechanical device configured to generate an amount of conductive substance during an operation of the mechanical device, wherein the conductive substance includes a ferromagnetic material,
    wherein a distance between the first electrode and the second electrode of the sensor is configured to be adjustable according to the amount of conductive substance generated during the operation of the mechanical device to which the sensor is attached,
    wherein at least one of the first electrode and the second electrode includes a magnetic member formed of a magnetic material,
    wherein the magnetic member is configured and arranged to cause the conductive substance including the ferromagnetic material to be accumulated between the first electrode and the second electrode of the sensor.

2. The system of claim 1, wherein conductive substance is accumulated between the first electrode and the second electrode.

3. The system of claim 2, wherein an end portion of one of the first electrode and the second electrode facing the other of the first electrode and the second electrode and facing toward a direction from which the conductive substance approaches thereto is chamfered.

4. The system of claim 2, wherein a resin material is filled in a region other than a region where the conductive substance is accumulated between the first electrode and the second electrode.

5. The system of claim 2, wherein the distance between the first electrode and the second electrode is a circumferential gap disposed between the first electrode and the second electrode,
    wherein one of the first electrode and the second electrode is an inner electrode and the other of the first electrode and the second electrode is an outer concentric electrode,
    wherein the circumferential gap is disposed between an outer circumferential surface of the inner electrode and an inner circumferential surface of the outer concentric electrode, and
    wherein the circumferential gap is configured and arranged to receive the conductive substance therein.

6. The system of claim 5, wherein the circumferential gap is disposed over the entire periphery of the outer circumferential surface of the inner electrode so as to surround the inner electrode.

7. The system of claim 5, wherein the magnetic member is configured and arranged to attract the conductive substance into the circumferential gap, and
    wherein the magnetic member is attached to one of the first electrode and the second electrode.

8. The system of claim 5, wherein the outer concentric electrode is a box-shaped electrode having a body with an interior space defined by an upwardly facing opening,
    wherein the inner electrode and the magnetic member are disposed centrally in the interior space of the box-shaped electrode and attached to the box-shaped electrode using a fastener.

9. The system of claim 8, wherein the sensor further comprises a resin material that is filled in the interior space of the box-shaped electrode other than regions with the circumferential gap, the magnetic member, the fastener and the inner electrode.

10. The system of claim 9, wherein the circumferential gap, as viewed in a cross sectional view of the sensor, is shallowly formed, and
    wherein the shallowly formed circumferential gap is configured and arranged to make it difficult for air bubbles to remain in the circumferential gap, and to smoothly carry out the accumulation of the conductive substance in the circumferential gap.

11. The system of claim 1, wherein at least one of the first electrode and the second electrode is replaceable.

12. The system of claim 11, wherein at least one of the first electrode and the second electrode is replaceable with an electrode having a different size, and
    wherein the distance between the first electrode and the second electrode is adjustable.

13. The system of claim 1, wherein one of the first electrode and the second electrode has a tapered surface facing the other of the first electrode and the second electrode.

14. The system of claim 13, wherein one of the first electrode and the second electrode is threadably attached to the other of the first electrode and the second electrode, and
    wherein a spring is provided between the first electrode and the second electrode.

15. The system of claim 14, wherein, when the threaded state of one of the first electrode and the second electrode is loosened, the other of the first electrode and the second electrode is moved by the spring in an extending direction of the spring.

16. The system of claim 1, wherein the detector is configured to detect the amount of conductive substance, which is generated during the operation of the mechanical device to which the sensor is attached, based on the change in the electric resistance between the first electrode and the second electrode due to the accumulation of the conductive substance between the first electrode and the second electrode.

17. A machinery comprising:
    a flange, a device being housed in the machinery, the device includes a case, the case being fixed to the flange in an airtight manner, and a sensor comprising:
- a first electrode;
- a second electrode; and
- a detector configured to sense a change in electric resistance between the first electrode and the second electrode when a voltage is applied between the first electrode and the second electrode, and wherein the sensor is attached to the device, wherein the device is configured to generate an amount of conductive substance during an operation of the device, wherein the conductive substance includes a ferromagnetic material, wherein a distance between the first electrode and the second electrode of the sensor is configured to be adjustable according to the amount of conductive substance generated during the operation of the device to which the sensor is attached, wherein at least one of the first electrode and the second electrode includes a magnetic member formed of a magnetic material, and wherein the magnetic member is configured and arranged to cause the conductive substance including the ferromagnetic material to be accumulated between the first electrode and the second electrode of the sensor.

18. The machinery of claim 17, wherein at least a portion of the case contacting the flange is formed of insulating material.

19. The machinery of claim 17, wherein the sensor is detachably fixed to the flange.

20. The machinery of claim 19, wherein an end surface of the case contacting the flange is threadably fixed to an end surface of the flange.

21. The machinery of claim 17, wherein the device is a speed reducer.

22. The machinery of claim 17, wherein the sensor is attached to the case.

* * * * *